US009489490B1

(12) United States Patent
Theobald

(10) Patent No.: US 9,489,490 B1
(45) Date of Patent: Nov. 8, 2016

(54) MOBILE ROBOT FOR RECEIVING, TRANSPORTING, AND/OR DELIVERING ONE OR MORE PHARMACEUTICAL ITEMS

(71) Applicant: Daniel Theobald, Sommerville, MA (US)

(72) Inventor: Daniel Theobald, Sommerville, MA (US)

( * ) Notice: Subject to any disclaimer, the term of this patent is extended or adjusted under 35 U.S.C. 154(b) by 25 days.

(21) Appl. No.: 13/872,362

(22) Filed: Apr. 29, 2013

(51) Int. Cl.
*G06F 7/00* (2006.01)
*G06F 19/00* (2011.01)
(52) U.S. Cl.
CPC .................................. *G06F 19/3462* (2013.01)
(58) Field of Classification Search
CPC .. G05D 1/024; G05D 1/0274; G05D 1/0255; G05D 1/0242; G05D 1/0225
See application file for complete search history.

(56) References Cited

U.S. PATENT DOCUMENTS

| 6,707,381 | B1 * | 3/2004 | Maloney | 340/568.1 |
| 8,935,005 | B2 * | 1/2015 | Rosenstein | B25J 11/009 700/245 |
| 2002/0039183 | A1 * | 4/2002 | Yagita | 356/240.1 |
| 2010/0234995 | A1 * | 9/2010 | Zini | G05B 19/41895 700/258 |

FOREIGN PATENT DOCUMENTS

JP          2004231357 A   *  8/2004

* cited by examiner

*Primary Examiner* — Yolanda Cumbess
(74) *Attorney, Agent, or Firm* — Albert J. Brunett

(57) ABSTRACT

Mobile robots and methods for operating mobile robots are provided. One of these mobile robots autonomously transports a pharmaceutical item from a first location to a second location. The mobile robot autonomously delivers the pharmaceutical item at the second location.

17 Claims, 7 Drawing Sheets

MOBILE ROBOT FOR RECEIVING, TRANSPORTING, AND/OR DELIVERING ONE OR MORE PHARMACEUTICAL ITEMS

CLAIM OF PRIORITY

This patent application claims priority to and is a continuation-in-part of U.S. patent application Ser. No. 13/587,098 filed Aug. 16, 2012 entitled "Method and Device for Accommodating Items" which is hereby incorporated herein by reference in its entirety

BACKGROUND OF THE INVENTION

1. Technical Field

The present disclosure relates generally to a mobile robot and, more particularly, to fulfilling an order for a pharmaceutical item.

2. Background Information

In a typical hospital setting, a doctor may order prescription medication for his/her patient. This order is communicated to the pharmacy of the hospital. Upon reviewing the order, a pharmacist may provide the prescription medication to a hospital runner for delivery to a nurse or the patient. The hospital runner, for example, may bring the prescription medication to the nurse who is assigned to administer the medication to the patient. However, such a hospital runner may take breaks during his/her shift that may delay the receipt of the medication by the nurse and, thus, the administration of the medication to the patient. In addition, it may be difficult for a hospital to find and retain qualified individuals to fulfill such runner positions and other similar positions.

There is a need in the art for an improved method for fulfilling an order for medication and/or other pharmaceutical items.

SUMMARY OF THE DISCLOSURE

Mobile robots and methods for operating mobile robots are provided. One of these mobile robots autonomously transports a pharmaceutical item from a first location to a second location. The mobile robot autonomously delivers the pharmaceutical item at the second location.

BRIEF DESCRIPTION OF THE DRAWINGS

The following detailed description will be better understood when read in conjunction with the appended drawings, in which there is shown one or more embodiments of the present disclosure. It should be understood, however, that the various embodiments of the present disclosure are not limited to the precise arrangements and instrumentalities shown in the drawings.

DETAILED DESCRIPTION

Figure 1:
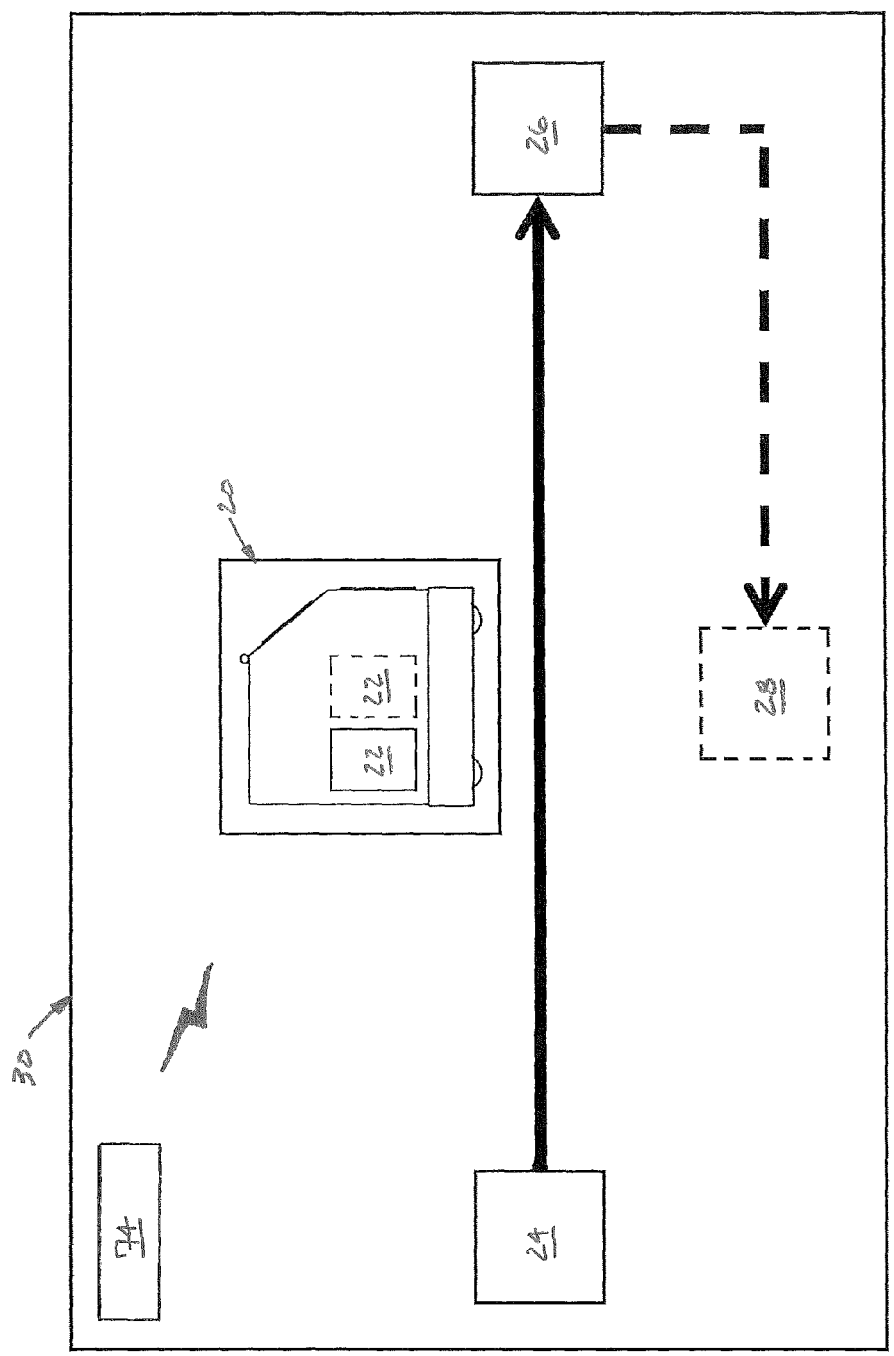
FIG. 1 is a schematic illustration a mobile robot fulfilling one or more pharmaceutical item orders at a patient care facility.

FIG. 1 illustrates a mobile robot 20 adapted to at least partially fulfill one or more orders for one or more pharmaceutical items 22. The mobile robot 20, for example, may receive the ordered pharmaceutical items 22 at at least one a pickup location 24. The mobile robot 20 may respectively transport these pharmaceutical items 22 from the pickup location 24 to one or more drop off locations 26 and 28; e.g., first and second drop off locations. The mobile robot 20 may subsequently deliver the pharmaceutical items 22 at the respective drop off locations 26 and 28.

The term "pharmaceutical item" may describe a topically, orally or intravenously administered medical substance for use in diagnosing, preventing, treating and/or curing a disease, virus, injury, disorder and/or deficiency of a patient; e.g., a human or an animal. An example of a pharmaceutical item 22 is prescription or over-the-counter medication such as, for example, an antibiotic, a vaccine, a cancer treatment, a hormone treatment and a pain suppressant. Another example of a pharmaceutical item 22 is a medical fluid such as, for example, saline, blood, platelets, and a radioactive or non-radioactive diagnostic fluid (e.g., a tracer fluid). Another example of a pharmaceutical item 22 is a dietary supplement such as, for example, a vitamin supplement, a mineral supplement, a fiber supplement, a fatty acid supplement and an amino acid supplement. Such a dietary supplement may be in a form of a pill or intravenous (IV) fluid. The mobile robot 20, of course, may receive, transport and/or deliver various types of pharmaceutical items 22 other than those described above.

The mobile robot 20 may be operated at a patient care facility 30 such as, for example, a hospital. Other examples of the patient care facility 30 include, but are not limited to, an emergency medical facility, a medical clinic or office, a mental treatment clinic or office, a physical rehabilitation (rehab) center or office, an addiction rehabilitation (rehab) center or office, and a veterinarian clinic or office. The patient care facility 30 may be located within a building, a complex of buildings, a subterranean structure, an encampment, a fort, a base, or an outpost. The patient care facility 30 may alternatively be located aboard a ship, a submersible, an aircraft, a spacecraft, or any other type of vehicle. The mobile robot 20, of course, may operate within, outside and/or near various types of patient care facilities other than those described above.

The mobile robot 20 may receive and deliver the pharmaceutical items 22 at various locations inside and/or outside of the patient care facility 30. The pickup location 24, for example, may be located at a pharmacy (e.g., a hospital pharmacy), a pharmaceutical storage area, or a pharmaceutical distribution area. One or more of the drop off locations may each be located at, for example, a patient room, a doctor office, a nurse station, a remote pharmacy station, or a cashier station. In another example, one or more of the drop off locations may each be located at another pharmacy, another pharmaceutical storage area, or another pharmaceutical distribution area. The mobile robot 20, of course, may receive and/or deliver the pharmaceutical items 22 at various locations other than those described above.

The mobile robot 20 may be configured as an autonomous mobile robot that performs one or more tasks without continuous outside control and/or intervention. The mobile robot 20, for example, may receive instructions to perform a certain task at a certain location such as, for example, to deliver a pharmaceutical item 22 to an individual such as a patient. The mobile robot 20 may subsequently determine and perform the operation(s) necessary to complete the task based on, for example, its current location, surrounding obstacles, its operating environment, the type of task to be performed, etc. The mobile robot 20 may also adapt to unknown, new and/or changing operating environments without additional outside control and/or intervention.

The mobile robot 20 may be fully autonomous during performance of one or more tasks. The mobile robot 20 may also or alternatively be semi-autonomous during performance of one or more tasks. The mobile robot 20 may also or alternatively be (e.g., remote) controlled by an operator (e.g., a human controller) during performance of one or more tasks.

The term "fully autonomous" may describe an apparatus that performs one or more tasks without, for example, any outside control and/or intervention. A fully autonomous mobile robot, for example, may perform a task without receiving instructions (e.g., vectors, commands, etc.) from a human operator during performance of the task.

The term "semi-autonomous" may describe an apparatus that performs one or more tasks without, for example, continuous outside control. A semi-autonomous mobile robot, for example, may perform a task utilizing one or more periodic instructions from an operator (e.g., a human controller) that bound and/or qualify the performance of the task. The instructions may provide, for example, an updated location of where the task is to be performed, identify an unknown obstacle, control the scope of the task, control when the task should be performed, etc.

Figure 2:
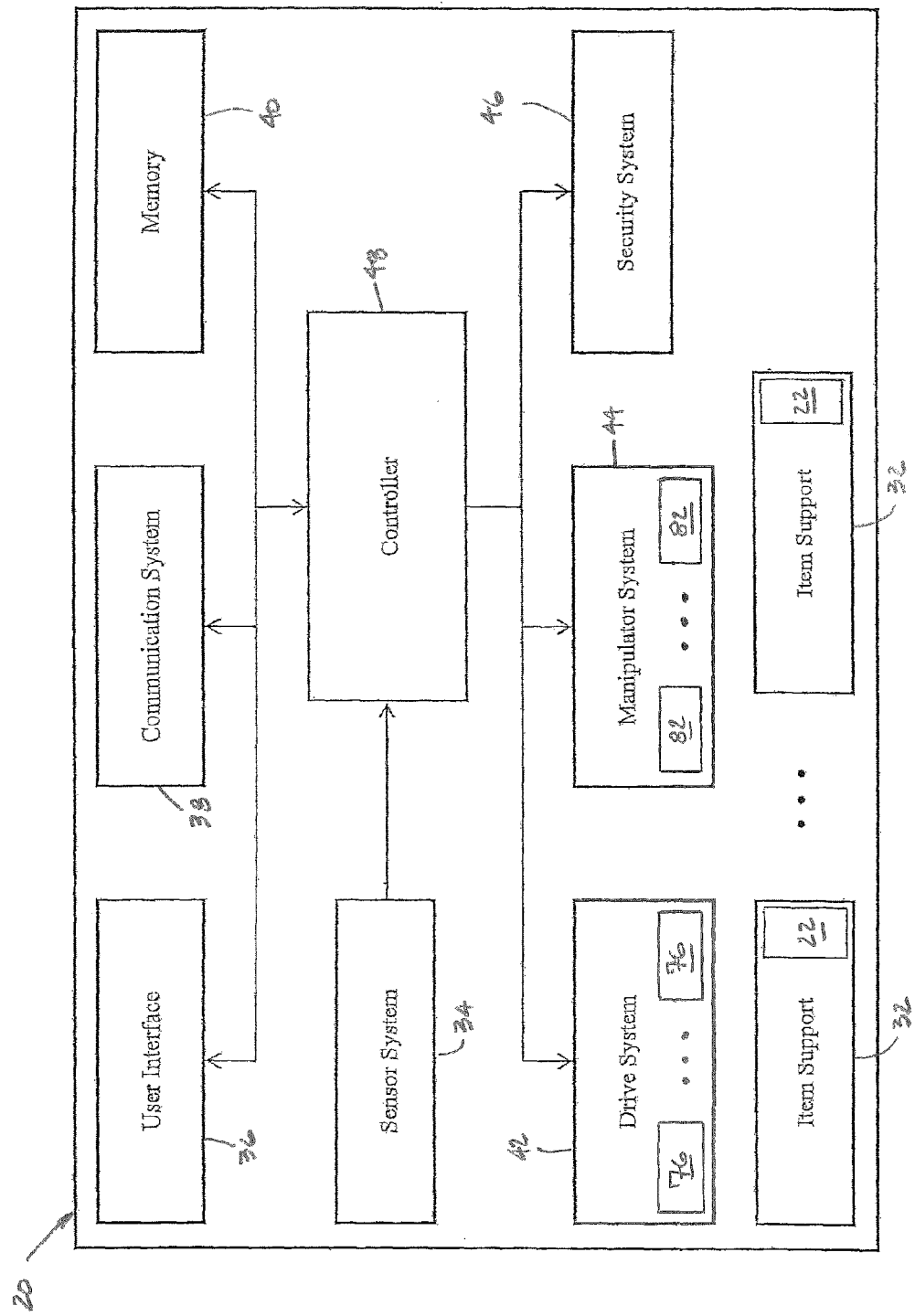
FIG. 2 is a block diagram of the mobile robot.

FIG. 2 is a block diagram of the mobile robot 20. The mobile robot 20 includes one or more item supports 32. The mobile robot 20 also includes a sensor system 34, a user interface 36, a communication system 38, memory 40, a drive system 42, a manipulator system 44, a security system 46, and a controller 48.

Figure 4:
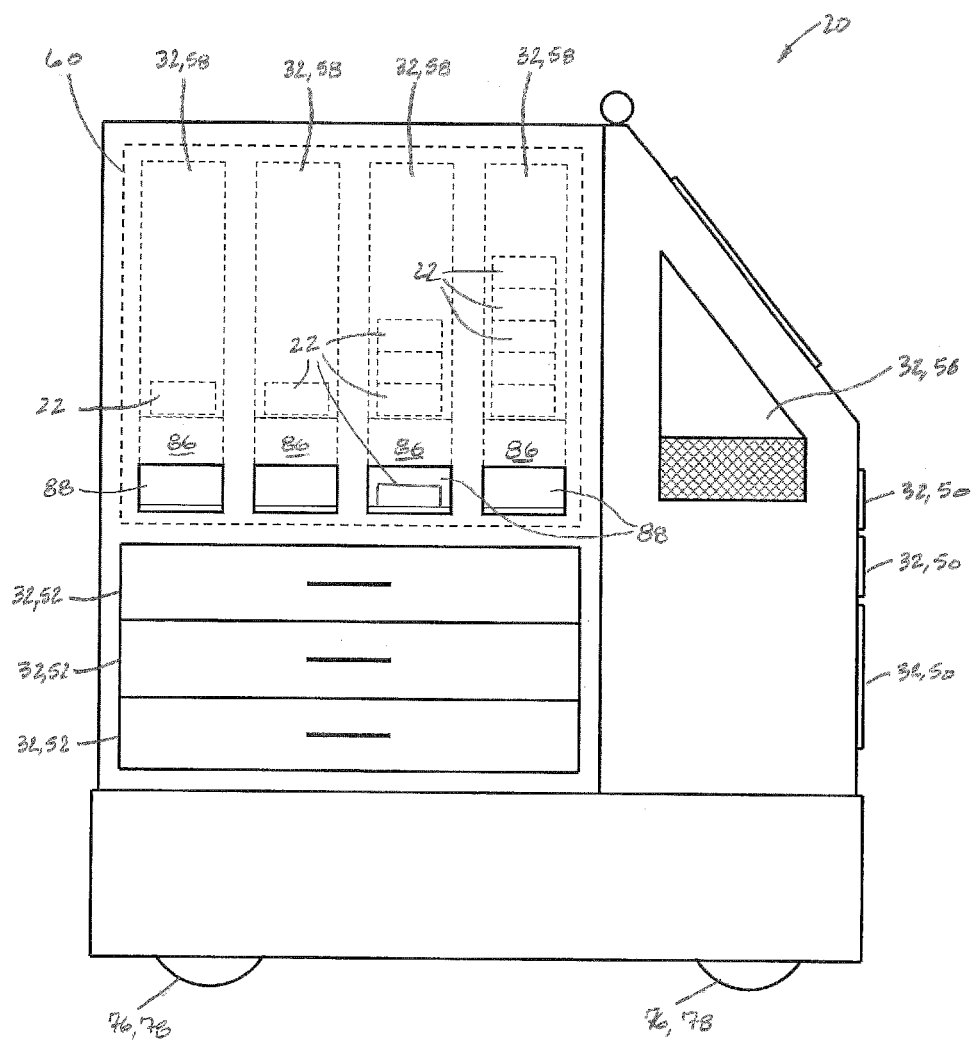
FIG. 4 is a side illustration of another embodiment of the mobile robot.
Figure 5:
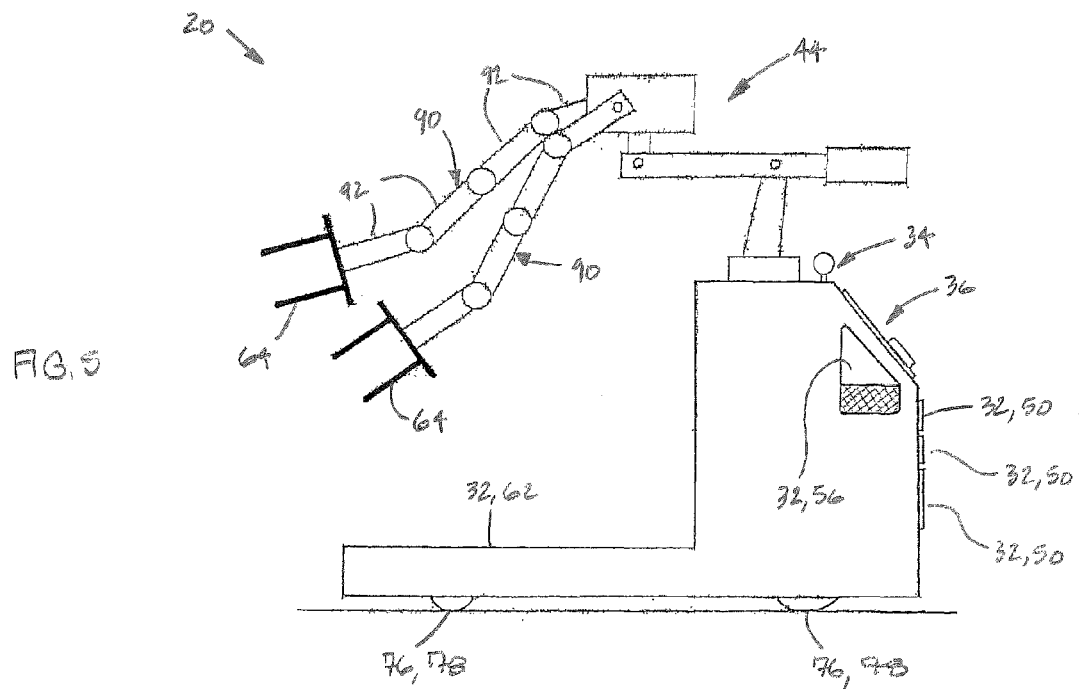
FIG. 5 is a side illustration of another embodiment of the mobile robot.
Figure 6:
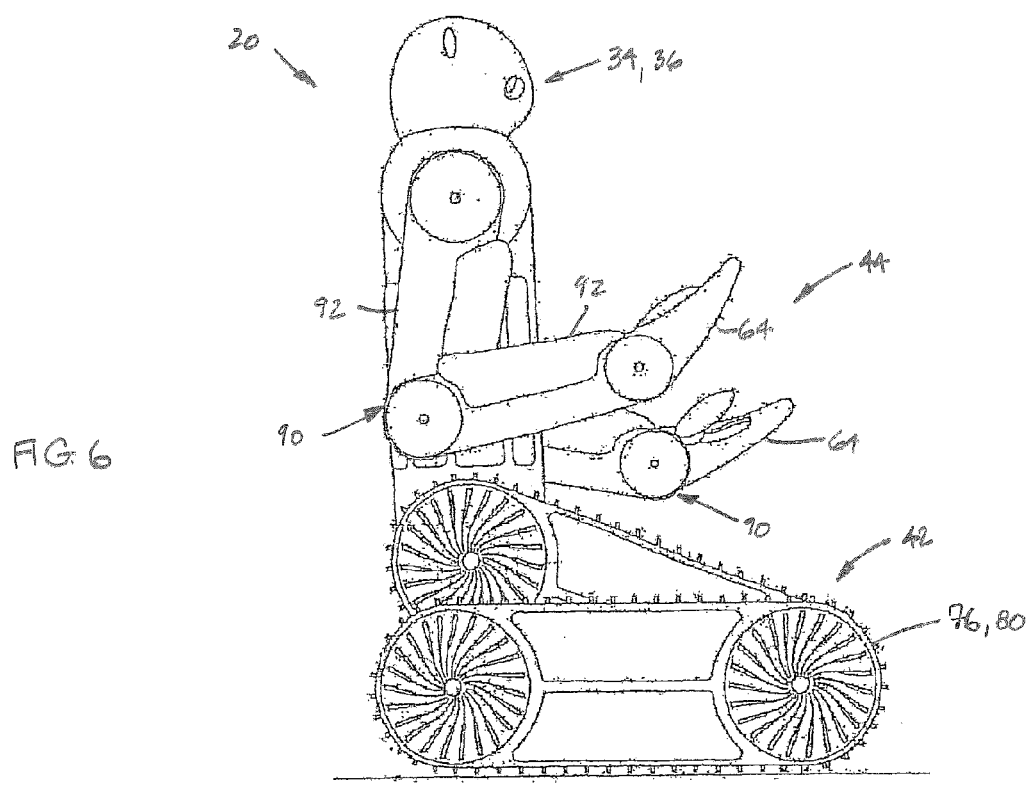
FIG. 6 is a side illustration of another embodiment of the mobile robot.

Each of the item supports 32 is adapted to securely or accessibly hold, contain and/or otherwise support one or more of the pharmaceutical items 22. For example, referring to FIG. 3, one or more of the item supports 32 may each be configured as a drawer 50 and 52 (e.g., cabinet drawer). One or more of the item supports 32 may each be configured as a shelf within (or a base of) a cabinet interior (e.g., a cubby), which may be opened and closed using at least one cabinet door 54. At least one of the item supports 32 may be configured as an exterior compartment 56 such as, for example, a cubby or a pocket. Referring to FIG. 4, one or more of the item supports 32 may each be configured as an internal compartment 58 for a component (e.g., a dispenser 60) of the manipulator system 44. Referring to FIG. 5, at least one of the item supports 32 may be configured as a platform 62 such as, for example, a deck or a bed. Referring to FIGS. 5 and 6, one or more of the item supports 32 may each be configured as a component (e.g., an end effector 64) of the manipulator system 44.

The mobile robot 20 may also or alternatively include various item supports 32 other than those described above and illustrated in the drawings. For example, the mobile robot 20 may include an item support configured as or arranged within a climate controlled (e.g., refrigerated) container. In this manner, the mobile robot 20 may transport or otherwise hold (e.g., perishable) medications or other pharmaceutical items 22 for a relatively long time between receiving and delivering the items 22. The mobile robot 20 therefore is not limited to any particular item support configurations.

Referring to FIGS. 1 and 2, the sensor system 34 is adapted to survey an operational environment of the mobile robot 20; e.g., room(s) and/or hallway(s) of the patient care facility 30. The sensor system 34 is also or alternatively adapted to receive location data indicative of a location of the mobile robot 20 and/or location(s) of other object(s) within its operating environment.

Figure 3:
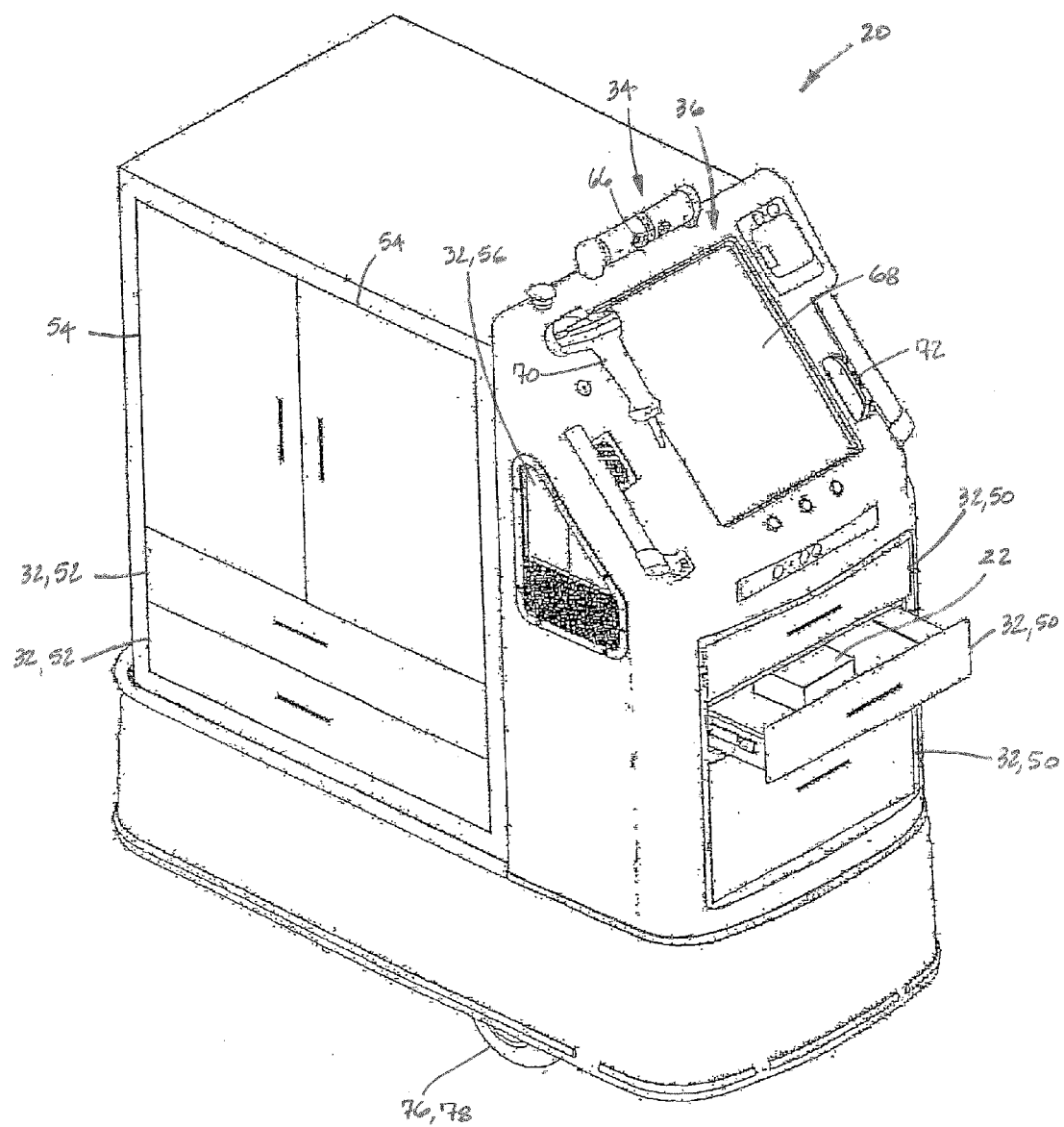
FIG. 3 is a perspective illustration of an embodiment of the mobile robot.

Referring to FIGS. 2 and 3, the sensor system 34 includes one or more locator sensors. These locator sensors may be operated to spatially locate (e.g., triangulate) the mobile robot 20 relative to, for example, its surrounding environment, its geographic location, and/or one or more locators (e.g., RF tags, physical landmarks, etc.). Examples of a locator sensor include, but are not limited to, a proximity sensor, a global positioning system (GPS) receiver, a radar system, an infrared system, a laser system, a radio transceiver, and a visual location system with at least one camera 66.

The user interface 36 is adapted to receive information from an individual such as, for example, a patient, a doctor, a nurse, a caregiver or a pharmacist. The user interface 36 is also adapted to present information to an individual. The user interface 36, for example, may visually and/or tactilely display a message to the individual. The user interface 36 may also or alternatively audibly reproduce a message for the individual.

The user interface 36 may include a display such as, for example, a visual display screen 68 (e.g., a liquid crystal display (LCD) screen), a tactile display device (e.g., a Braille display), or a printer (e.g., a laser printer, an inkjet printer, a thermal printer, etc.). The user interface 36 may include an electro-acoustic transducer such as, for example, an audio speaker and/or a microphone connected to a voice control system. The user interface 36 may include a security device such as, for example, a bio-information sensor, a voice recognition system, a barcode scanner 70, a microchip (e.g., security chip) reader, a card reader 72, etc. Examples of a bio-information sensor include, but are not limited to, an eye retinal sensor, a fingerprint sensor and a handprint sensor. The user interface 36 may also or alternatively include a camera (e.g., the camera 66), a touch screen (e.g., the screen 68), a keypad, a keyboard, and/or any other type of user interface device.

Referring to FIGS. 1 and 2, the communication system 38 is adapted to receive data from at least one remote computer system 74. The communication system 38 is also or alternatively adapted to send data to at least one remote computer system 74. The communication system 38 may include a cellular, satellite and/or radio receiver and a cellular, satellite and/or radio transmitter.

Referring to FIG. 2, the memory 40 may be a non-transitory computer readable medium, and configured to store software (e.g., program instructions) for execution by the controller 48. The memory 40 may include a volatile memory and/or a nonvolatile memory. Examples of a volatile memory may include a random access memory (RAM) such as a dynamic random access memory (DRAM), a static random access memory (SRAM), a synchronous dynamic random access memory (SDRAM), a video random access memory (VRAM), etc. Examples of a nonvolatile memory may include a read only memory (ROM), an electrically erasable programmable read-only memory (EEPROM), a computer hard drive, etc.

Referring to FIGS. 1 and 2, the drive system 42 is adapted to move the mobile robot 20 within its operating environment; e.g., inside and/or outside of the patient care facility 30. The drive system 42 includes one or more motorized and/or steerable propulsion devices 76. One or more of the propulsion devices 76 of FIGS. 3 to 5 are each configured as a plurality of motorized drive wheels 78. One or more of the propulsion devices 76 of FIG. 6 are each configured as a motorized (e.g., robotic and multi-linkage) track system 80. The drive system 42 may also or alternatively include one or more propulsion devices with configurations other than those described above and illustrated in the drawings.

Referring to FIG. 2, the manipulator system 44 includes one or more manipulators 82. One or more of these manipulators 82 may be adapted to move, or assist with the movement of, one or more of the pharmaceutical items 22 onto or into one or more of the item supports 32. One or more of the manipulators 82 may be adapted to move, or assist with the movement of, one or more of the pharmaceutical items 22 off or out of one or more of the item supports 32. One or more of the manipulators 82 may also or alternatively be adapted to distribute, or assist with the distribution of, one or more of the pharmaceutical items 22 from one or more of the item supports 32.

Figure 7:
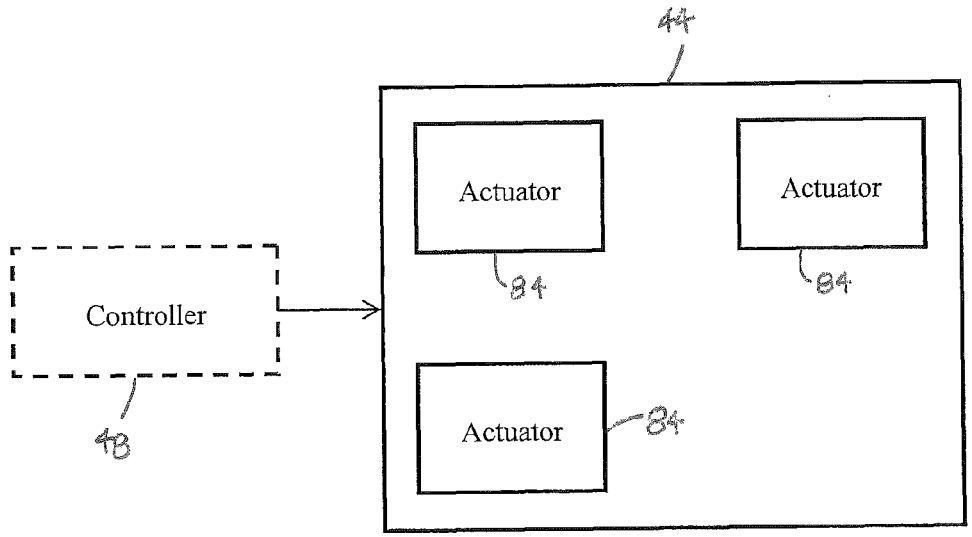
FIG. 7 is a block diagram of a portion of a manipulator system for the mobile robot of FIG. 3.

Referring to FIGS. 3 and 7, one or more of the manipulators 82 may each be configured as a robotic drawer. Each robotic drawer includes a respective one of the drawers 50 and at least one actuator 84, which is adapted to open and/or close the drawer 50. Examples of an actuator 84 include, but are not limited to, an electric motor, a hydraulic or pneumatic pump, and a hydraulic cylinder.

One or more of the drawers 52 may each be configured as a robotic drawer. One or more of the cabinet doors 54 may each be configured as a robotic cabinet door. For example, each drawer 52 may be opened and/or closed by at least one respective actuator. Each cabinet door 54 may be opened and/or closed by at least one respective actuator. Alternatively, one or more of the drawers 50 and/or 52 and/or one or more of the cabinet doors 54 may each be configured as a manual drawer or cabinet door.

Referring to FIG. 4, one or more of the manipulators 82 may each be configured as a component 86 of the pharmaceutical item dispenser 60. This dispenser component 86 is adapted to dispense or otherwise direct and/or release one or more of the pharmaceutical items 22 from a respective one of the internal compartments 58 to an external compartment 88; e.g., an open bin. The dispenser component 86 may include rollers that may grip and move a pharmaceutical item 22. The dispenser component 86 may also or alternatively include a dispenser door connected to at least one actuator. This actuator may open and/or close the dispenser door to permit at least one of the pharmaceutical items 22 to move from the internal compartment 58 to the external compartment 88.

The pharmaceutical item dispenser 60 may have various configurations other than those described above and illustrated in the drawings. For example, the pharmaceutical item dispenser 60 may include one or more dispenser components from any type of consumable or electronic item vending machine. In another example, the pharmaceutical item dispenser 60 may be configured as a pick-and-place machine. Such a pick-and-place machine may include a two, three or more axis manipulator that picks one of the pharmaceutical items 22 from one of the internal compartments 58, and disposes the picked item 22 into one of the external compartments 88.

Referring to FIGS. 5 and 6, one or more of the manipulators 82 may each be configured as a robotic manipulator arm 90. Each manipulator arm 90 may be electronically, hydraulically, pneumatically and/or mechanically actuated. Each manipulator arm 90 includes the end effector 64, which is connected to one or more arm members 92 (e.g., linkages). Examples of an end effector include, but are not limited to, a gripping device, a suction device, an electromagnet, a winch, a clasp, etc.

The manipulator system 44 may also or alternatively include various types of manipulators 82 other than those described above and illustrated in the drawings. For example, one or more of the manipulators 82 may each be configured as a pallet jack, a lift platform, a conveyor system, a slide carriage or a crane. Other examples of manipulators are disclosed in U.S. Pat. No. 7,902,784, U.S. Pat. No. 7,719,222 and U.S. Pat. No. 7,348,747, each of which is hereby incorporated herein by reference in its entirety.

Figure 8:
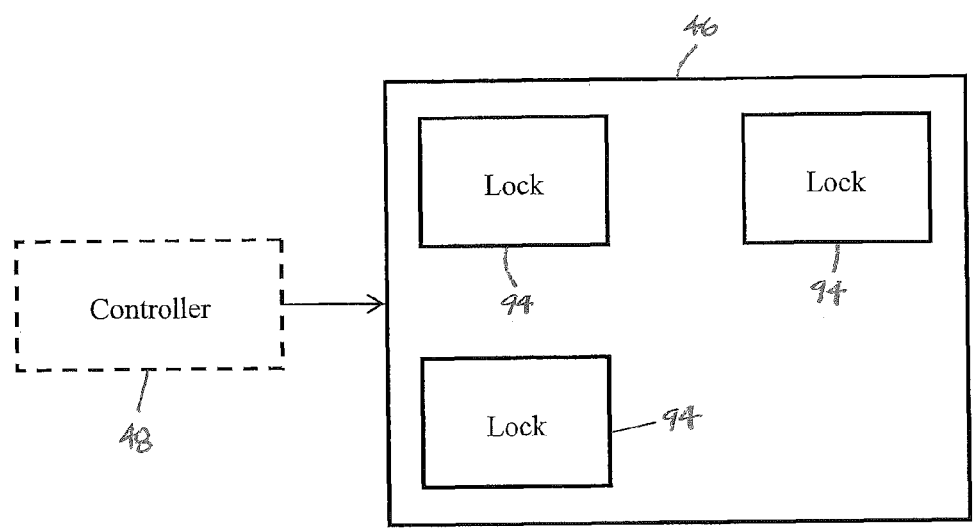
FIG. 8 is a block diagram of a portion of a security system for the mobile robot of FIG. 3.

Referring to FIGS. 2, 3 and 8, the security system 46 is adapted to secure the pharmaceutical item(s) 22 with (e.g., on or within) at least one of the item supports 32. The security system 46, for example, may include one or more electronically, hydraulically, pneumatically and/or mechanically actuated locks 94 such as, for example, a bolt or a latch. One or more of these locks 94 may each be adapted to secure (e.g., lock) a respective one of the drawers 50 in a closed position. In this manner, un-authorized individuals may be unable to access the pharmaceutical item(s) 22 within the drawers 50. Similarly, one or more of the drawers 52 and/or one or more of the cabinet doors 54 may also or alternatively each be securable (e.g., held closed) with at least one electronically, hydraulically, pneumatically and/or mechanically actuated lock.

Referring to FIGS. 5 and 6, the security system 46 may include one or more of the end effectors 64. For example, each end effector 64 may grip a pharmaceutical item 22 to secure that item 22. Each end effector 64 may subsequently release the gripped pharmaceutical item 22 to provide access to the item 22. The pharmaceutical item 22 may be released, for example, by reducing clamping pressure on the item 22. Alternatively, the pharmaceutical item 22 may be released by disengaging (e.g., letting go of or dropping) the item 22.

Referring to FIG. 2, the security system 46 may also or alternatively include one or more security devices other than those described above and illustrated in the drawings. For example, the security system 46 may include one or more manually operated locks; e.g., a key lock, a combination lock, a pad lock, etc.

The controller 48 is in signal communication (e.g., hardwired or wirelessly connected) with the sensor system 34, the user interface 36, the communication system 38, the memory 40, the drive system 42, the manipulator system 44 and the security system 46. The controller 48 may be implemented with hardware, or a combination or hardware and software. The controller 48 may include one or more single or multi-core processors, analog and/or digital circuitry, etc.

Figure 9:
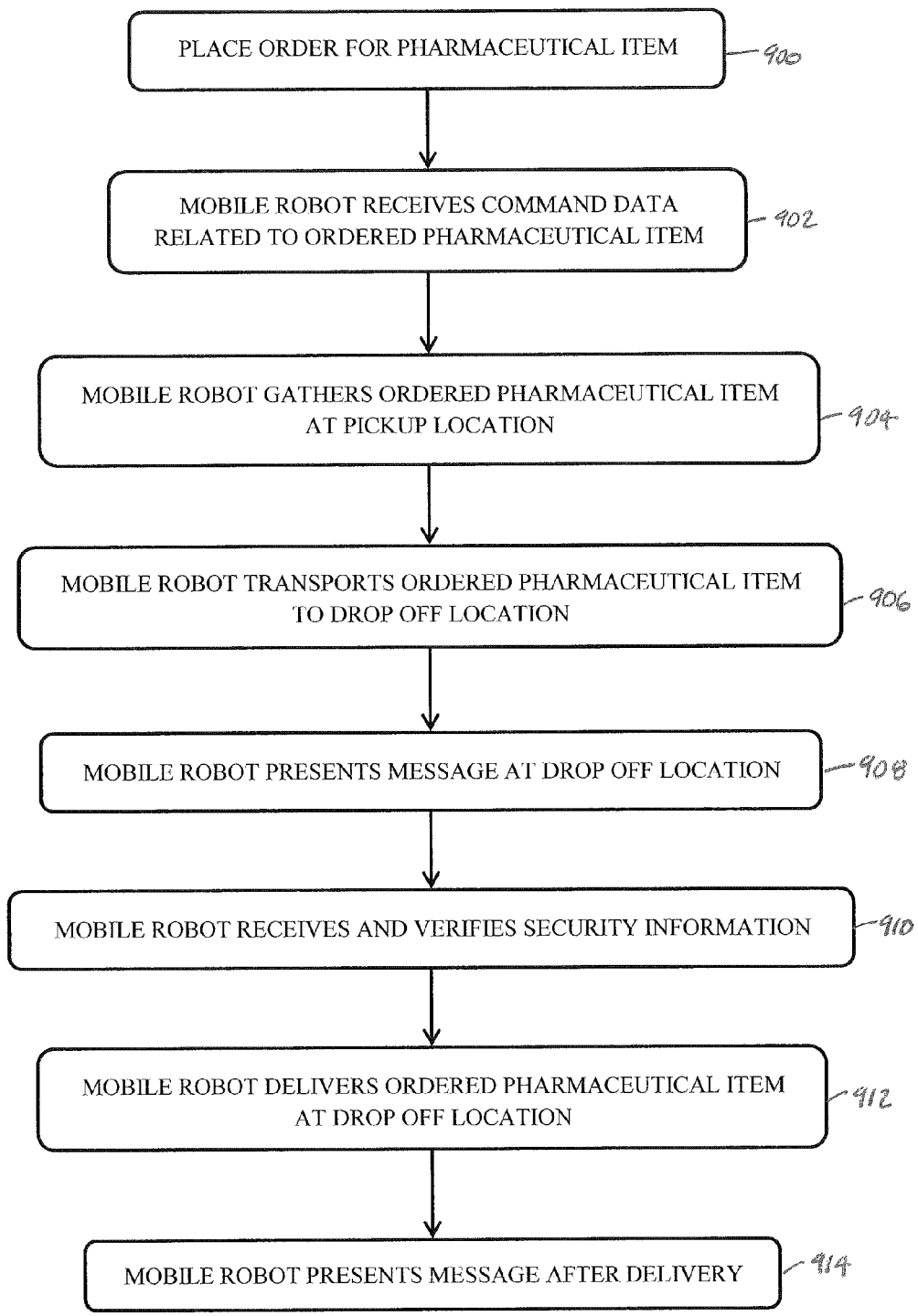
FIG. 9 is a flow diagram of a method for fulfilling at least one order for at least one pharmaceutical item utilizing the mobile robot and a remote computer system.

FIG. 9 is a flow diagram of a method for fulfilling at least one order for at least one pharmaceutical item 22. This method is described below as being performed at a hospital utilizing the mobile robot 20 of FIG. 1 and at least one remote computer system 74. Examples of such a computer system 74 include, but are not limited to, a kiosk, a personal computer (e.g., a desktop or laptop computer), a tablet computer, a mobile telephone (e.g., a smart phone), a personal digital assistant (PDA), and a central computer system. The method of FIG. 9, of course, may be performed in various patient care facilities other than a hospital. In addition, this method may be performed with various participants and pharmaceutical items 22 other than those described below.

In step 900, an order is placed for at least one pharmaceutical item 22 to be delivered to the drop off location 26. This order may be placed by an individual through the computer system 74, which subsequently directly or indirectly communicates data related to the order to the mobile robot 20. Alternatively, the order may be placed by an individual through the user interface 36 of the mobile robot 20.

The order may include various types of information related to the pharmaceutical item 22. For example, the order may identify a location of where and/or a time of when the pharmaceutical item 22 is to be delivered. The order may identify the individual placing the order. The order may identify a recipient(s) of the pharmaceutical item 22. The order may assign a priority to the delivery of the pharmaceutical item 22. The order may identify the specific type (e.g., brand, lot number, etc.) of the pharmaceutical item 22 to be delivered. The information included with the order, of course, is not limited to the foregoing examples.

In an exemplary embodiment, a doctor (or any other healthcare professional) may place the order by inputting a prescription for medication for a patient into the computer system 74. The doctor may also input a request (e.g., instructions) for the prescribed medication to be delivered to the drop off location 26 for administration to the patient.

The delivery request may include a time at which the medication is to be delivered to drop off location 26, which may be based on when the medication is to be administered to the patient. The delivery request may also include a priority indicator. For example, the doctor may designate medication (or another pharmaceutical item) for a patient in a critical care ward with a relatively high priority indicator. By contrast, the doctor may designate medication (or another pharmaceutical item) for a patient in general care ward with a relatively low priority indicator.

The computer system 74 may generate command data related to (e.g., indicative of) the prescribed medication and/or the delivery request. The command data, for example, may be generated based on the ordered medication, the time at which the medication is to be delivered, and/or the priority indicator. The command data may also be generated based on information related to the patient such as, for example, a location of the patient within the hospital, scheduled appointments for the patient, and/or security criteria.

The security criteria may include patient security criteria and/or recipient security criteria. The patient security criteria may include a patient social security number (SSN), a patient name, a patient date of birth, a patient password, and/or data relating to a patient fingerprint or retinal scan. The patient security criteria may also or alternatively include information provided on a patient identification device such as, for example, a wristband or identification (ID) card configured with a barcode and/or a chip.

The recipient security criteria may include similar information as that described above with respect to the patient security criteria. The recipient security criteria, however, is directed towards an individual (e.g., a nurse or caregiver) that may receive the ordered medication for the patient and/or administer the medication to the patient. The command data, of course, is not limited to any particular types of security criteria.

The command data may include scheduling data, inventory data and/or security data. The scheduling data may be indicative of when the mobile robot 20 is to gather the medication from the pickup location 24 and/or when the mobile robot 20 is to deliver the medication to the drop off location 26. The scheduling data may also be indicative of other tasks the mobile robot 20 is to perform (e.g., delivering medication to other patients), and/or priority indicators for one or more of those other tasks. The inventory data may be indicative of the types, ingredients, contents, masses or weights, and/or dimensions of the medication (pharmaceutical item) to be delivered. The security data may be indicative of one or more of the security criteria.

The computer system 74 may transmit the command data to the mobile robot 20 over a wireless and/or wired network. Alternatively, the computer system 74 may transmit the command data to an intermediate computer system (e.g., a central computer system). The intermediate computer system may subsequently relay at least some of the command data to the mobile robot 20. Alternatively, the intermediate computer system may transmit derivative command data to the mobile robot 20 that is related to the command data and, thus, the order. The derivative command data may include, for example, information related to a plurality of orders, including the order of the step 900, as well as a priority in which those orders are to be fulfilled.

In step 902, the mobile robot 20 receives the command data. The controller 48, for example, may receive the command data through the communication system 38. Alternatively, the controller 48 may receive the command data from the user interface 36. The doctor, for example, may place the order for the medication utilizing the user interface 36 during the step 900 rather than the computer system 74.

In step 904, the mobile robot 20 gathers the ordered pharmaceutical item 22 (e.g., the medication). The controller 48, for example, may signal the drive system 42 to autonomously move the mobile robot 20 to the pickup location 24 based on signals received from the sensor system 34 and/or the command data (e.g., scheduling data). The pickup location 24 may be located at a hospital pharmacy, or any other location within the hospital that stores or otherwise distributes the medication ordered in the step 900.

At the pickup location 24, the controller 48 may signal the manipulator system 44 to open one of the drawers 50. The controller 48 may also signal the user interface 36 to electronically present a message to a staff member (e.g., a pharmacist) of the hospital. This message may ask (e.g., instruct) the staff member to respectively load the ordered medication into the open drawer 50. Once the ordered medication is within the drawer 50, the controller 48 may receive instructions through the user interface 36 from the staff member to close and/or secure the drawer 50 using the manipulator system 44 and/or the security system 46. Alternatively, the controller 48 may close and/or secure the drawer 50 upon receiving a signal from the sensor system 34 that the medication has been loaded into the drawer 50 and/or the staff member is clear of the drawer 50. In this manner, unauthorized individuals (e.g., other patients, etc.) may be unable to access the ordered medication.

In step 906, the mobile robot 20 transports the ordered pharmaceutical item 22 (e.g., the medication) to the drop off location 26. The controller 48, for example, may signal the drive system 42 to autonomously move the mobile robot 20 to the drop off location 26 based on signals received from the sensor system 34 and/or the command data (e.g., scheduling data). The drop off location 26 may be located at a nurse station that services the patient for which the medication was ordered. Alternatively, the drop off location 26 may be located within the patient room or any other place within the hospital (i.e., the patient care facility 30).

In step 908, the mobile robot 20 visually, audibly and/or tactilely presents a message at the drop off location 26. The controller 48, for example, may signal the user interface 36 to visually present a message to a nurse at the nurse station using the display screen 68. This message may provide the nurse instructions on how to access the ordered medication. For example, the message may indicate in which drawer 50 the medication is located. The message may also or alternatively indicate how the nurse may identify himself/herself to the mobile robot 20 as an authorized recipient of the medication. Other examples in which a message may be presented are disclosed in U.S. patent application Ser. No. 13/851,314 entitled "Mobile Robot for Delivering an Item and Presenting a Message Related to the Item", which is hereby incorporated herein by reference in its entirety.

In step 910, the mobile robot 20 receives and verifies security information. The nurse, for example, may swipe his/her identification (ID) card through the card reader 72 in response to seeing/hearing the message presented in the step 908. The controller 48 may receive data from the user interface 36 indicative of a nurse identification encoded on the ID card. The controller 48 may subsequently compare the encoded nurse identification to one or more nurse identifications for nurses who are authorized to work at the nurse station and/or to administer medication to the patient. The mobile robot 20, of course, may use various security techniques other than those described above to verify the identity of the nurse. For example, the mobile robot 20 may receive a name from the nurse, and/or an audible/typed alphanumeric password from the nurse. The mobile robot 20 may also or alternatively scan a finger, a hand, an eye retinal and/or another body part of the nurse, etc.

In step 912, the mobile robot 20 delivers the ordered pharmaceutical item 22 at the drop off location 26. In particular, the mobile robot 20 delivers the ordered medication to the nurse where, for example, the security information provided by the nurse satisfies the security criteria. The controller 48, for example, may signal the security system 46 and/or the manipulator system 44 to unlock and/or open the drawer 50 to provide the nurse access to the ordered medication.

In step 914, the mobile robot 20 visually, audibly and/or tactilely presents another message at the drop off location 26, for example, after delivering the ordered pharmaceutical item 22. The controller 48, for example, may signal the user interface 36 to visually present a message to a nurse at the nurse station using the display screen 68. This message may inquire as to whether the nurse (e.g., the recipient of the pharmaceutical item 22) has any questions and/or whether the nurse needs any additional assistance. If the nurse does not have any questions and/or does not need any additional assistance, the nurse may utilize the user interface 36 to dismiss the mobile robot 20. However, if the nurse has a question(s) or needs assistance, the nurse may use the user interface 36 to call or page, for example, the prescribing doctor or any other individual. Such a step may be particularly useful, for example, where the mobile robot 20 delivers the pharmaceutical item 22 to the patient for self administration.

In some embodiments, the mobile robot 20 may take an image of the recipient of the order pharmaceutical item 22 (e.g., the nurse, etc.) using the camera 66. The image may be taken before delivering the pharmaceutical item 22 in order to verify the recipient is the intended recipient (e.g., nurse or patient) using, for example, facial recognition. The image may also or alternatively be taken during and/or after the delivery to record who actually received the pharmaceutical item 22. Similarly, a voice of the recipient may be recorded before, during and/or after delivery of the pharmaceutical item 22 to verify the recipient's identity and/or keep a record of the recipient. The mobile robot 20, of course, may use various security techniques other than those described above to verify the recipient as the intended recipient and/or record mobile robot transactions.

In some embodiments, the mobile robot 20 may track a chain of custody of one or more of the ordered pharmaceutical items 22. The mobile robot 20, for example, may record information related to and/or identify one or more of the following individuals:

an individual (e.g., a pharmacist) who loads or otherwise sends the ordered pharmaceutical item(s) 22 at the pickup location 24;

an individual who accesses or tampers with the ordered pharmaceutical item(s) 22 and/or the respective item support(s) 32 during transit; and an individual (e.g., a nurse or patient) who unloads or otherwise receives the ordered pharmaceutical item(s) 22 at the drop off location 26, 28.

For example, the mobile robot 20 may take an image and/or a voice recording of one or more of the foregoing individuals. The mobile robot 20 may subsequently identify one or more of these individuals using image and/or voice recognition software. The mobile robot may also or alternatively record a username and/or password of one or more of the individuals.

The mobile robot 20 may also or alternatively track various other types of information related to the ordered pharmaceutical item(s) 22 and/or its chain of custody. The mobile robot 20, for example, may record and/or track information related to one or more of the following:

who ordered the pharmaceutical item(s) 22;

when the pharmaceutical item(s) 22 were ordered;

when the pharmaceutical item(s) 22 were received at the pickup location 24;

when the pharmaceutical item(s) 22 were delivered at the drop off location 26, 28;

a username and/or password of the individual loading and/or sending the pharmaceutical item(s) 22;

a username and/or a password of the individual accessing, unloading and/or receiving the pharmaceutical item(s) 22; and/or contents of the pharmaceutical item(s) 22.

By tracking the chain of custody of the pharmaceutical item(s) 22 and/or recording individuals who interact with the mobile robot 20, the mobile robot 20 may be used to reduce "shrinkage". The term "shrinkage" may describe the misplacement and/or theft of the pharmaceutical item(s) 22; e.g., controlled medication. The tracking and recording capabilities of the mobile robot 20, for example, may deter theft of the pharmaceutical item(s) 22.

The tracking and recording capabilities of the mobile robot 20 may also be used to reduce human error such as, for example, a pharmacist sending the wrong medication to a patient. For example, where the mobile robot 20 tracks the contents of the medication, the controller 48 may compare the contents of the pharmaceutical item(s) 22 received at the pickup location 24 to those identified in the original order. In addition, by verifying the recipient of the pharmaceutical item(s) 22, the mobile robot 20 may reduce the likelihood of the item(s) 22 being delivered to the wrong recipient; e.g., a first patient receiving a second patient's medication.

In some embodiments, the mobile robot 20 may autonomously deliver the ordered pharmaceutical item using the pharmaceutical item dispenser 60 of FIG. 4. In such embodiments, commonly ordered pharmaceutical items 22 may be pre-loaded into the internal compartments 58 such that the mobile robot 20 does not need to gather the items 22 at the pickup location 24 for each order. One or more of the pharmaceutical item(s) 22, of course, may alternatively be loaded into the internal compartment(s) 58 as needed. At the drop off location 26, the controller 48 may signal the dispenser component 86 to direct one of the pharmaceutical items 22 from a respective one of the internal compartment 58 to the external compartment 88 where it may be accessed by an individual; e.g., a nurse or patient.

In some embodiments, the mobile robot 20 may autonomously gather and/or autonomously deliver the pharmaceutical item 22 using one or more of the manipulator arms 90 of FIG. 5. In this manner, the mobile robot 20 may gather and/or deliver the pharmaceutical item 22 without aid from an individual such as, for example, the pharmacist or the nurse. For example, the controller 48 may signal the manipulator system 44 to pick up and move the medication with one or more of the manipulator arms 90 using signals received from the sensor system 34 and/or command data received through the communication system 38. The controller 48 may subsequently signal the manipulator system 44 to place the medication into or onto a respective one of the item supports 32; e.g., into the drawer 50. Similarly, the controller 48 may signal the manipulator system 44 to deliver the ordered medication.

In some embodiments, a pharmaceutical distribution robot (e.g., a pick-and-place machine) may autonomously load the ordered pharmaceutical item(s) onto/into the items support(s) 32 of the mobile robot 20. The pharmaceutical distribution robot, for example, may be arranged with a pharmaceutical distribution (e.g., pharmacy) station at the pickup location 24. The pharmaceutical distribution robot may include a robotic arm or a multi-axis manipulator that loads one or more of the pharmaceutical items 22 onto/into at least one of the item supports 32. The pharmaceutical distribution robot may be self-controlled, or operated by a human operator. The pharmaceutical distribution robot may alternatively be remotely controlled by the controller 48, or another remote computer system (e.g., the computer system 74).

In some embodiments, a pharmaceutical distribution robot (e.g., a pick-and-place machine) may autonomously receive the ordered pharmaceutical item(s) from the mobile robot 20. The pharmaceutical distribution robot, for example, may be arranged with a pharmaceutical distribution (e.g., remote pharmacy) station at a respective drop off location. The pharmaceutical distribution robot may include a robotic arm or a multi-axis manipulator that unloads one or more of the pharmaceutical items 22 from at least one of the item supports 32. The pharmaceutical distribution robot may be self-controlled, or operated by a human operator. The pharmaceutical distribution robot may alternatively be remotely controlled by the controller 48, or another remote computer system (e.g., the computer system 74).

In some embodiments, the mobile robot 20 may fulfill a plurality of pharmaceutical item orders using the method of FIG. 9. For example, the mobile robot 20 may receive a plurality of pharmaceutical items 22 at the pickup location 24 (or multiple pickup locations) for one or more of the orders. The mobile robot 20 may subsequently deliver the ordered pharmaceutical item(s) 22 at the first drop off location 26 on the way to delivering the ordered pharmaceutical item(s) 22 at the second drop off location 28. Alternatively, the mobile robot 20 may receive and deliver the pharmaceutical item(s) 22 for one of the orders before receiving and delivering the pharmaceutical item(s) 22 for another one of the orders. Still alternatively, the mobile robot 20 may receive and/or deliver the pharmaceutical item(s) 22 for one of the orders during fulfillment of another one of the orders.

The foregoing pharmaceutical item orders may be placed substantially contemporaneously or serially by one or more individuals; e.g., doctors, nurses, pharmacists, caregivers, patients, etc. The orders may be scheduled for fulfillment by the mobile robot 20 using one or more scheduling criteria. Examples of the scheduling criteria include, but are not limited to, the following:

priority indicators for one or more of the ordered pharmaceutical items;
when the orders were placed;
when the command data for the orders was received by the mobile robot;
where the ordered pharmaceutical items are located for pickup;
where the ordered pharmaceutical items are to be delivered;
where the mobile robot is currently located, or is scheduled to be located;
distance between respective pickup and drop off locations;
travel time between respective pickup and drop off locations;
identity of who placed the order (e.g., a doctor vs. a patient);
pharmaceutical item classification such as, for example, whether a respective pharmaceutical item is hazardous (e.g., radioactive), combustible, etc.;
storage requirements for the pharmaceutical item such as, for example, whether a respective pharmaceutical item requires refrigeration; and/or
cost of the pharmaceutical items.

For example, the controller 48 (or another computer system) may schedule delivery of a pharmaceutical item 22 at the first drop off location 26 (e.g., a nurse station in an emergency room) before delivery of a pharmaceutical item 22 at the second drop off location 28 (e.g., a patient room) where the first item has a higher priority indicator. In another example, the controller 48 (or another computer system) may schedule delivery of a pharmaceutical item 22 at the first drop off location 26 before delivery of a pharmaceutical item 22 at the second drop off location 28 where the first drop off location 26 is located on the same floor of the hospital as the pickup location 24, whereas the second drop off location 28 is located on another floor. The present disclosure, of course, is not limited to the foregoing examples.

In some embodiments, the mobile robot 20 may be adapted to charge its power storage device(s) (e.g., batteries) during and/or between performance of one or more of its tasks. For example, the mobile robot 20 may dock at a charging station to charge its power storage device(s), or swap its depleted power storage device(s) for charged power storage device(s). The mobile robot may also or alternatively include a wireless energy receiver that receives energy from a wireless energy transmitter. Examples of a wireless energy receiver and a wireless energy transmitter are disclosed in U.S. patent application Ser. No. 13/773,689 entitled "Wirelessly Transferring Energy to a Mobile Device" which is hereby incorporated herein by reference in its entirety.

The mobile robot 20 may navigate and/or interact with various objects, devices and/or individuals within the patient care facility 30, or any other operating environment, other than those described above. The mobile robot 20, for example, may open and/or close a door using the manipulator system 44, or by signaling a remote controlled actuator for the door through the communication system 38. The mobile robot 20 may control and/or ride an elevator or any other type of transportation device to move between floors or areas at the facility 30. The mobile robot 20 may interact with emergency medical services (EMS) personnel; e.g., receive/deliver the pharmaceutical item(s) 22 or any other item from/to the EMS personnel. The mobile robot 20 may also or alternatively transport patient(s) around the patient care facility 30. For example, the mobile robot 20 may push and/or pull a gurney or a wheel chair through the facility 30. In another example, the mobile robot 20 may physically carry a patient using the manipulator system 44 (e.g., the manipulator arms 90), or on a chair or bed configured with the mobile robot 20.

The mobile robot 20 of course may receive, transport and/or deliver various items other than those described above. The mobile robot, for example, may transport and deliver a patient aid device to an individual. Examples of a patient aid device include, but are not limited to, a wheel chair, a gurney, crutch(es), a cane and a brace. The mobile robot 20 may transport and deliver luggage. The mobile robot may also or alternatively transport patients or other individuals at (e.g., inside and/or outside) the patient care facility 30.

It is to be understood that the terminology used herein is used for the purpose of describing specific embodiments, and is not intended to limit the scope of the present invention. It should be noted that as used herein, the singular forms of "a", "an" and "the" include plural references unless the context clearly dictates otherwise. In addition, unless defined otherwise, all technical and scientific terms used herein have the same meaning as commonly understood by one of ordinary skill in the art to which this invention belongs.

Although the description above contains many specific examples, these should not be construed as limiting the scope of the embodiments of the present disclosure, but as merely providing illustrations of some of the presently preferred embodiments of the present invention. It will be appreciated by those skilled in the art that changes could be made to the embodiments described above without departing from the broad inventive concept thereof. It is to be understood therefore that this disclosure is not limited to the specific embodiments disclosed herein, but it is intended to cover modifications within the spirit and scope of the embodiments of the present disclosure. Accordingly, the present invention is not to be restricted except in light of the attached claims and their equivalents.

What is claimed is:

1. A method for operating a mobile robot, comprising:
   autonomously transporting a pharmaceutical item from a first location to a second location using the mobile robot; and
   autonomously delivering the pharmaceutical item at the second location using the mobile robot
   wherein the pharmaceutical item is disposed within an item support of the mobile robot; and
   wherein the delivering of the pharmaceutical item comprises opening the item support using a manipulator system of the mobile robot.

2. The method as defined in claim 1, wherein the mobile robot delivers the pharmaceutical item to one of an individual and a station at the second location.

3. The method as defined in claim 1, further comprising at least partially tracking a chain of custody of the pharmaceutical item using the mobile robot.

4. The method as defined in claim 1, wherein the delivering of the pharmaceutical item further comprises moving the pharmaceutical item using a manipulator arm of the mobile robot.

5. The method as defined in claim 1, further comprising:
   receiving command data through a component of the mobile robot, the command data related to a prescription for the pharmaceutical item; and
   autonomously moving the mobile robot to the first location to receive the pharmaceutical item based on the command data.

6. The method as defined in claim 1, further comprising:
   securing the pharmaceutical item with the mobile robot using a component of the mobile robot to prevent an unauthorized individual from accessing the secured pharmaceutical item;
   wherein the delivering of the pharmaceutical item comprises providing an authorized individual access to the secured pharmaceutical item using at least the component.

7. The method as defined in claim 1, further comprising:
   locking the pharmaceutical item within the item support of the mobile robot using a component of the mobile robot;
   wherein the delivering of the pharmaceutical item comprises at least unlocking the item support using the component.

8. The method as defined in claim 1, further comprising:
   transporting a second pharmaceutical item to a third location using the mobile robot; and
   delivering the second pharmaceutical item at the third location using the mobile robot;
   wherein the pharmaceutical item comprises a first pharmaceutical item, and the mobile robot delivers the first pharmaceutical item before delivering the second pharmaceutical item based on priority criteria for at least one the first and the second pharmaceutical items.

9. The method as defined in claim 1, wherein the pharmaceutical item comprises one of oral medication, topical medication, intravenous medication, a medical fluid and a dietary supplement.

10. The method as defined in claim 1, wherein one of the first location and the second location is located at a hospital pharmacy.

11. A method involving a mobile robot, comprising:
    receiving command data through a component of the mobile robot, the command data related to an order for a pharmaceutical item;
    receiving the pharmaceutical item with the mobile robot at a first location; and
    transporting the pharmaceutical item from the first location to a second location using the mobile robot based on the command data;
    wherein the mobile robot receives the pharmaceutical item from a pharmaceutical distribution robot at the first location;

wherein the component comprises a communication system that receives the command data from a remote computer system;

wherein the computer system comprises one of a kiosk, a personal computer, a tablet computer, a mobile telephone, a personal digital assistant and a central computer system; and wherein the method further comprises
generating the command data with the computer system based on the order;
and communicating the command data from the computer system to the communication system.

12. The method as defined in claim 11, wherein the component comprises a user interface.

13. The method as defined in claim 11, wherein the mobile robot receives the pharmaceutical item at the first location using a manipulator system.

14. The method as defined in claim 11, further comprising autonomously delivering the pharmaceutical item at the second location using a manipulator system.

15. An apparatus for at least partially fulfilling an order for a pharmaceutical item, the apparatus comprising:

a mobile robot comprising a climate controlled container, a drive system and a controller; the climate controlled container comprising an item support adapted to receive the pharmaceutical item at a first location; and the controller adapted to receive command data related to the order for the pharmaceutical item, and further adapted to signal the drive system to move the item support from the first location to a second location for delivery of the pharmaceutical item based on the command data.

16. The method as defined in claim 1, wherein the item support comprises a robotic drawer.

17. The method as defined in claim 1, wherein the item support comprises a robotic cabinet door.

* * * * *